United States Patent [19]

John

[11] 4,115,563
[45] Sep. 19, 1978

[54] PHARMACEUTICAL STEROID FORMULATION

[75] Inventor: Phillip Merrill John, East Greenbush, N.Y.

[73] Assignee: Sterling Drug Inc., New York, N.Y.

[21] Appl. No.: 777,317

[22] Filed: Mar. 14, 1977

[51] Int. Cl.² ............................................. A61K 31/58
[52] U.S. Cl. .................................... 424/241; 424/242; 424/243
[58] Field of Search .................... 424/241, 243, 242

[56] References Cited

U.S. PATENT DOCUMENTS

| 3,135,743 | 6/1964 | Clinton et al. | 260/239.55 |
| 3,296,255 | 1/1967 | Clinton et al. | 260/239.55 |
| 3,424,842 | 1/1969 | Nurnberg | 424/227 |
| 3,704,295 | 11/1972 | Clinton | 260/239.55 |

Primary Examiner—Elbert L. Roberts
Attorney, Agent, or Firm—Thomas L. Johnson; B. Woodrow Wyatt

[57] ABSTRACT

A pharmaceutical formulation comprising from 5 to 80 percent by weight of a pharmaceutically active steroid, 1 to 8 percent by weight of sodium starch glycolate and the remainder conventional excipients. A preferred specific embodiment is a capsule blend containing 4,4,17-trimethylandrosta-2,5-dieno-[2,3-d]isoxazole.

10 Claims, No Drawings

PHARMACEUTICAL STEROID FORMULATION

BACKGROUND OF THE INVENTION

1. Field of the Invention

This invention relates to a novel formulation containing a pharmaceutically active steroid.

2. Description of the Prior Art

Sodium starch glycolate, commercially available under the tradenames Primogel and Explotab, has been proposed as a disintegrating agent for tablet formulations. Sodium starch glycolate has been used as an adjuvant in aspirin tablets [Cid et al., J. Pharm. Belg. 26(1), 38–48 (1971)] and in phenobarbital tablets [Jaminet et al., Pharm. Acta Helvetiae 44, 418–432 (1969)].

SUMMARY OF THE INVENTION

In its composition of matter aspect, the invention relates to a pharmaceutical formulation comprising 5 to 80 percent by weight of a pharmaceutically active steroid, 1 to 8 percent by weight of sodium starch glycolate and the remainder conventional excipients.

In its process aspect, the invention relates to a process for preparing said formulation which comprises wet granulating the steroid with conventional excipients, drying the granulation until it contains less than 1 percent of water, and blending the granulation with a mixture of the sodium starch glycolate and conventional excipients.

DETAILED DESCRIPTION INCLUSIVE OF PREFERRED EMBODIMENTS

The invention is applicable to any steroid having pharmaceutical utlity, especially those having hormonal or endocrinological activity upon oral administration to animal organisms. Such steroids include estrogens, e.g. estrone, estradiol, etc.; andorgens, e.g. testosterone, dihydrotestosterone, etc.; progestins, e.g. progesterone, ethynyltestosterone, etc.; corticoids, e.g. cortisone, prednisolone, etc.

Particularly preferred steroids are the following: 4,4,17-trimethylandrosta-2,5-dieno[2,3-]isoxazol-17β-ol (I) (interceptive agent, U.S. Pat. Nos. 3,135,743 and 3,966,926); 17-methylandrostano[3,2-c]pyrazol-17β-ol (II) (stanazolol, anabolic agent, U.S. Pat. 3,704,295); 17-ethynylandrosta-2,4-dieno[2,3-d]isoxazol-17β-ol (III) (danazol, pituitary gonadotrophin inhibitor, U.S. Pat. No. 3,135,743) and 4α, 5-epoxy-17β-hydroxy-3-oxo-5α-androstane-2α-carbonitrile (IV) (adrenal inhibitor, U.S. Pat. No. 3,296,255). The structural formulas of these steroids are as follows:

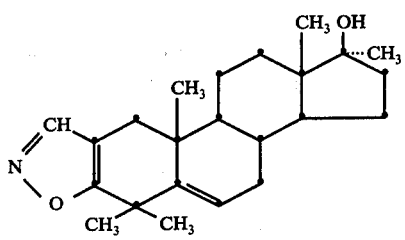

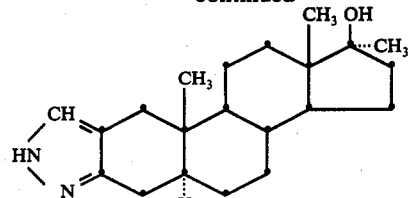

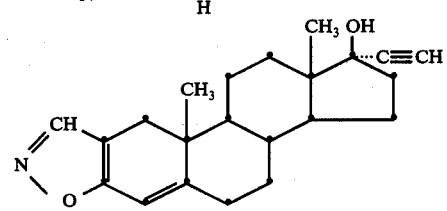

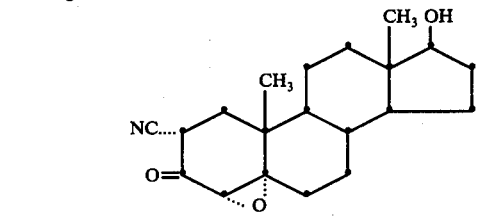

The steroid can be present in the formulation in amounts ranging from about 5 to about 80 percent by weight of the total formulation, depending on the biological potency and intended use of the steroid.

The sodium starch glycolate can be present in the formulation in amounts ranging from about 1 to about 8 percent by weight of the total formulation and is independent of the amount of steroid present.

A particular aspect of the invention relates to a capsule blend comprising from 5 to 65 percent by weight of the pharmaceutically active steroid, 1 to 8 percent by weight of sodium starch glycolate and the remainder conventional excipients. The preferred conventional excipients used in the capsule blend are starch, lactose, fumed silicon dioxide and magnesium stearate.

The formulation is prepared by granulation and densifying procedures. In the event that a wet granulation of the steroid and conventional excipients is employed, it is essential that the granulation be dried thoroughly, until the granulation has less than 1 percent water, before the sodium starch glycolate is added, otherwise a mixture of very porous granules of low density is obtained.

The following examples will further illustrate the invention without the latter being limited thereby.

EXAMPLE 1

A mixture of:

250 parts 4,4,17-trimethylandrosta-2,5-dieno[2,3-d]isoxazol-17β-ol
47 parts starch (USP)
50 parts lactose (hydrous, USP)
3 parts fumed silicon dioxide (Cab-O-Sil)
is passed twice through a No. 24 screen and then mixed for five minutes in a blender. Water (200 parts) is slowly incorporated into the mixture until a damp mass is formed. The material is then passed through a No. 4 screen and 18 parts additional water added. The mixture is spread on a tray and allowed to dry until less than one percent of water is present (overnight at 50° C.). To the resulting dry granulation is added a mixture of:

20 parts sodium starch glycolarte (Explotab; Edward Mendell Co., Inc., Carmel N.Y.).
10 parts lactose (hydrous, USP)
19 parts starch (USP)
1 part magnesium stearate (USP)
and the total mixture blended and placed in gelatin capsules containing 400 mg per capsule (250 mg of steroid per capsule).

Capsules prepared by the foregoing procedure were tested for disintegration time by immersion into 250 ml. of tenth normal hydrochloric acid at 37° C. under conditions of mild agitation. The contents of the capsule readily disintegrated in six to eight minutes' time. On the other hand, capsules prepared according to the foregoing procedure, except that the sodium starch glycolate was omitted, failed to disintegrate in tenth normal hydrochloric acid at 37° C.; the gelatin capsule was seen to dissolve away leaving behind a pasty plug of material that failed to disperse.

Capsules prepared according to Example 1 were placed on stability test. After three months at 25° and 50° C., thin layer chromatography showed less than 2% decomposition of the steroid, and capsules held for three months at 25° C. showed a disintegration time of 14–17 minutes.

The 4,4,17-trimethylandrosta-2,5-dieno[2,3-d]isoxazol-17β-ol in Example 1 can be replaced by other pharmaceutically active steroids, for example, 17-methylandrostano[3,2-c]pyrazol-17β-ol, 17-ethynylandrosta-2,4-dieno[2,3-d]isoxazol-17β-ol, and 4α,5-epoxy-17β-hydroxy-3-oxo-5α-androstane-2α-carbonitrile to obtain the corresponding capsule blends.

EXAMPLE 2

A granulation prepared from:

30 parts 4,4,17-trimethylandrosta-2,5-dieno-[2,3-d]isoxazol-17β-ol
245 parts starch (USP)
245 parts lactose (hydrous, USP)
5 parts fumed silicon dioxide (Cab-O-Sil)
is blended with a mixture of 30 parts sodium starch glycolate
15 parts lactose (hydrous, USP)
28.5 parts starch (USP)
1.5 parts magnesium stearate (USP)
according to the procedure of Example 1, and placed in gelatin capsules containing 600 mg. per capsule (30 mg. of steroid per capsule).

Capsules prepared according to Example 2 showed a disintegration time of six minutes.

The capsule blends of Examples 1 and 2 were tested for their effectiveness in disrupting pregnancy in female rats as compared with the steroid alone, according to the procedure described in U.S. Pat. No. 3,966,926. The results showed that the steroid alone and the two capsule blends were equally effective in disrupting pregnancy in the rat, at a dose level of 12–24 mg per kg of steroid.

EXAMPLE 3

A mixture of:

500 parts 4,4,17-trimethylandrosta-2,5-dieno-[2,3-d]isoxazol-17β-ol
100 parts dicalcium phosphate (USP)
25 parts starch (USP)
is blended and wet granulated with 20 parts of starch as 15% aqueous paste and with water as required, and the granulation is dried and reduced by oscillation to 16-mesh material. To the latter is added a mixture of:
15 parts sodium starch glycolate
7 parts starch (USP)
3 parts magnesium stearate and the total mixture is blended together to produce a formulation which is suitable for compression to produce tablets weighing about 670 mg. and containing 500 mg. of steroid.

I claim:

1. A solid pharmaceutical formulation comprising from 5 to 80 percent by weight of a pharmaceutically active steroid, 1 to 8 percent by weight of sodium starch glycolate and the remainder conventional excipients.

2. A formulation according to claim 1 wherein the steroid is a member of the group consisting of 4,4,17-trimethylandrosta-2,5-dieno[2,3-d]isoxazol-17β-ol, 17-methylandrostano[3,2-c]pyrazol-17β-ol, 17-ethynylandrosta-2,4-dieno[2,3-d]-isoxazol-17β-ol and 4α,5-epoxy-17β-hydroxy-3-oxo-5α-androstane-2α-carbonitrile.

3. A formulation according to claim 2 wherein the steroid is 4,4,17-trimethylandrosta-2,5-dieno[2,3-d]isoxazol-17β-ol.

4. A capsule blend according to claim 1 comprising from 5 to 65 percent by weight of a pharmaceutically active steroid, 1 to 8 percent by weight of sodium starch glycolate and the remainder conventional excipients.

5. A capsule blend according to claim 4 wherein the steroid is a member of the group consisting of 4,4,17-trimethylandrosta-2,5-dieno[2,3-d]isoxazol-17β-ol, 17-methylandrostano[3,2-c]pyrazol-17β-ol, 17-ethynylandrosta-2,4-dieno[2,3-d]-isoxazol-17β-ol and 4α,5-epoxy-17β-hydroxy-3-oxo-5α-androstane-2αcarbonitrile.

6. A capsule blend according to claim 5 wherein the steroid is 4,4,17-trimethylandrosta-2,5-dieno[2,3-d]isoxazol-17β-ol.

7. A capsule blend according to claim 6 wherein the conventional excipients are starch, lactose, fumed silicon dioxide and magnesium stearate.

8. A process for preparing a formulation according to claim 1 which comprises wet granulating the steroid with conventional excipients, drying the granulation until it contains less than 1 percent of water, and blending the granulation with a mixture of the sodium starch glycolate and conventional excipients.

9. A process according to claim 8 wherein the steroid is a member of the group consisting of 4,4,17-trimethylandrosta-2,5-dieno[2,3-d]isoxazol-17β-ol, 17-methylandrostano[3,2-c]-pyrazol-17β-ol, 17-ethynylandrosta-2,4-dieno[2,3-d]isoxazol-17β-ol and 4α,5-epoxy-17β-hydroxy-3-oxo-5α-androstane-2α-carbonitrile.

10. A process according to claim 8 wherein the steroid is 4,4,17-trimethylandrosta-2,5-dieno[2,3-d]isoxazol-17β-ol.

* * * * *